United States Patent [19]
Ellis et al.

[11] Patent Number: 5,204,426
[45] Date of Patent: Apr. 20, 1993

[54] COMMAND-CURABLE COMPOSITION

[75] Inventors: John Ellis, East Molesey; Alan D. Wilson, Liphook, both of England

[73] Assignee: National Research Development Corporation, London, England

[21] Appl. No.: 784,083

[22] Filed: Oct. 30, 1991

Related U.S. Application Data

[63] Continuation-in-part of Ser. No. 510,221, Apr. 18, 1990, abandoned.

Foreign Application Priority Data

Apr. 27, 1989 [GB] United Kingdom ............... 8909614

[51] Int. Cl.$^5$ ..................... C08F 30/02; C08L 43/02
[52] U.S. Cl. ..................... 526/278; 524/547; 523/116
[58] Field of Search ............ 524/123, 124, 125, 444, 524/494, 547; 523/116; 526/278

[56] References Cited

U.S. PATENT DOCUMENTS

| | | | |
|---|---|---|---|
| 4,067,927 | 1/1978 | Weil | 524/124 |
| 4,082,722 | 4/1978 | Schmitt et al. | 524/444 |
| 4,758,612 | 7/1988 | Wilson et al. | 523/116 |
| 4,824,876 | 4/1989 | Matsumoto et al. | 523/116 |
| 4,937,144 | 6/1990 | Podszun et al. | 523/116 |
| 5,068,298 | 11/1991 | Engelhardt et al. | 524/547 |

FOREIGN PATENT DOCUMENTS

| | | |
|---|---|---|
| 0241277 | 10/1987 | European Pat. Off. |
| 0340016 | 11/1989 | European Pat. Off. |
| 982577 | 2/1965 | United Kingdom |

OTHER PUBLICATIONS

Patent Abstracts of Japan vol. 8 No. 241 Nov. 6, 1984 and JP-A-59 122 410, (Tokyama Soda K.K.).
Patent Abstracts of Japan vol. 8 No. 11 Jan. 18, 1984, and JP-A-58 177 907 (Tokyama Soda K.K.).

*Primary Examiner*—Paul R. Michl
*Assistant Examiner*—LaVonda DeWitt
*Attorney, Agent, or Firm*—Nixon & Vanderhye

[57] ABSTRACT

A phosphonate ester (vinyl phosphonic acid reacted with equimolar diol) will cure on command (e.g. exposure to light) in the presence of an initiator. By adding inert filler, poly(vinyl phosphonic acid), ion-leachable glass powder and water, a command-curable dental cement with glass ionomer characteristics is obtained.

13 Claims, No Drawings

COMMAND-CURABLE COMPOSITION

This is a continuation-in-part of application Ser. No. 07/510,221, filed Apr. 18, 1990, now abandoned.

This invention relates to compositions curable on command, e.g. by the action of incident energy e.g. light (ultraviolet or visible) or ultrasound or a chemical initiator. Such compositions may contain inert or reactive fillers, in which case they can be classed as cements, and may be particularly useful in surgical, especially dental, applications.

As dental cements, glass ionomers as described in for example GB Patents 1422337 and 1484454 have attained wide popylarity for their compressive strength, their inherent adhesion to tooth material, their relatively fast setting time and their anti-caries action. However, a drawback in clinical practice is that, once mixed, the glass ionomer cement composition stays workable for a strictly limited time only, and sets rapidly.

According to the present invention, a command-curable composition comprises a phosphonate ester, being equivalent to the reaction product between an unsaturated (e.g. vinyl) phosphonic acid and a polyhydric alcohol in the mole ratio (0.2-2.0) phosphonic acid groups: 1 hydroxyl groups, plus an initiator suitably a light-activated initiator system or a chemical initiator system, plus a cross-linkable polymeric acid capable of being gelled by cations with a valency of at least 2, the acid containing on average one phosphonic acid group per one to three backbone carbon atoms. The said mole ratio is preferably (0.5-1.5):1 such as (0.8-1.2):1. The hydroxyls in the polyhydric alcohol are preferably interconnected via from two to twenty such as two to six carbon atoms, with oxygen atoms optionally interposed at least (preferably) every fifth carbon atom; the polyhydric alcohol is preferably a diol e.g. bis-(2-hydroxyethyl) ether (1,5-dihydroxy-3-oxa-pentane).

Optionally the composition additionally comprises any one or more of cation-leachable (e.g. aluminosilicate) glass powder, amphoteric or basic metal oxide (e.g. MgO), poly(vinyl phosphonic acid), and water; in the absence of both poly(vinyl phosphonic acid) and water, the glass powder could be replaced by an inert filler e.g. quartz. By "poly(vinyl phosphonic acid)" we include any cross-linkable polymeric acid capable of being gelled by cations with a valency of at least 2the acid containing on average one phosphonic acid group per one to three backbone carbon atoms. A minor proportion of poly(carboxylic acid) such as poly(acrylic acid) may also be present.

In the case of a chemically activated initiator system, its components (unlike the light-initiated case) must be kept separate until the composition is to be cured.

The invention extends to a pack comprising two separated pastes which when mixed form a curable composition as set forth above; the first paste may be the acid(s) plus water and the light-activated initiator system, and the second paste may be the glass powder suspended in the phosphonate ester. If the two pastes have been formulated to appropriate concentrations, one could in use squeeze out equal lengths of paste from two tubes, or scoop out equal numbers of spoonfuls from two tubs, as an easy way to ensure that the mixture is of the correct composition.

The glass powder preferably consists of particles substantially all of which are smaller than 100 microns, preferably smaller than 60 microns. The Si:Al range of 0.6-2:1 yields an opaque product, which may be acceptable in appropriate cases, but 0.2-0.6:1 can also be used. In place of glass, MgO deactivated at at least 900° C. may be used.

The invention also extends to a pack comprising the components of the curable composition set forth above, so packed that when unpacked and mixed they form the composition.

The invention will now be described by way of example.

Various esters of vinyl phosphonic acid

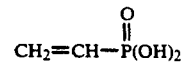

with polyhydric alcohols were formed, using the reaction of a precursor of this acid (vinyl phosphonic dichloride) with the alcohol in the presence of water, thus:

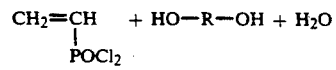

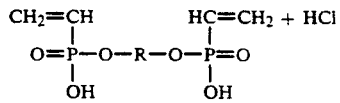

R = —C$_{2-6}$— with optional intervening oxygens e.g.
—C$_2$H$_4$—O—C$_2$H$_4$— or
—C$_2$H$_4$— or —nC$_4$H$_8$— or

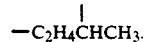

We term this reaction product a divinylphosphonic acid ester (DVPA ester).

Preferably, an intervening oxygen is provided after at most five consecutive carbon atoms. Thus, R(OH)$_2$ may (in addition) be butane 1,3 diol, pentane 1,5 diol, neopentylglycol, or H(OCH$_2$CH$_2$)$_n$OH having a molecular weight of 200–600, i.e. n=7 to 20 (approximately).

The DVPA ester can be induced to polymerize by the action of suitable initiator systems, a polymerisation taking place through the vinyl groups, like the dimethacrylate resins currently used in other dental restorative materials. Since the DVPA ester has two vinyl groups, crosslinking will also occur. The acid groups contained by DVPA ester confer water solubility on it.

These DVPA esters were mixed with visible-light-activated initiators. (camphorquinone CQ, plus ethyl dimethylaminobenzoate EDMAB, plus sodium p-toluenesulphinate NaTS) and exposed to visible light. They cured within 60 seconds to hard, water resistant materials. The presence of water in the DVPA ester did not prevent setting, although a high proportion of water resulted in softer materials initially, but which set over a longer period (about 1 hour). Similarly the presence of glass powder in the DVPA ester/water mix had no effect on the curing of the materials.

In the foregoing reaction, it will be appreciated that the ratio of (dibasic) vinylmonophosphonic acid molecules CH$_2$=CH—PO(OH)$_2$ or CH$_2$=CH—POCl$_2$ molecules to dihydric alcohol molecules can be varied; where this ratio is >1:1, i.e. the degree of esterification is correspondingly less than 100%, some acid function will remain on the DVPA ester. When, as in the reaction scheme above, the ratio is 2:1, the degree of esterification will be 50% and the other 50% of the acid OH groups remain. This can be expressed more generally in terms of the ratio between phosphonic acid groups —PO(OH)$_2$ and alcohol —OH groups: when this ratio is 1:1, the degree of esterification will be 50% DVPA ester in the presence of suitable initiators and activators will form a crosslinked polymer still containing some acid groups. In addition, in the presence of an ion-leachable glass and a poly(vinyl phosphonic acid), acid-base reactions will also occur. The presence of a water-soluble oxygen-containing unsaturated phosphonated monomer (i.e. the ester) has the useful additional effect of slowing down the acid-base (PVPA-glass) reaction, which is normally too fast unless other measures are taken, e.g. heat-deactivation of the glass.

EXAMPLE 1

Vinyl phosphonyl chloride was reacted with half the number of moles of bis-(2-hydroxyethyl)ether to form DVPA ester

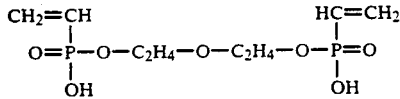

This DVPA ester was mixed with CQ+EDMAB+-NaTS (as light-activated initiators), to form a composition according to the invention, and exposed to 60 seconds' white light. The resulting cement was hard and resistant to water.

In an identical example except that the composition also included a minor proportion of water, similar results were obtained.

EXAMPLE 2

A composition was made up consisting of 4 parts by weight of the ester of Example 1, water (1 part), an aluminosilicate glass powder (8 parts) and CQ+EDMAB+NaTS. The glass is prepared by mixing together 437 parts by weight silica, 230 parts by weight alumina, 129 parts by weight calcium fluoride, 175 parts by weight cryolite and 29 parts by weight aluminium phosphate and heating to 1300° C. for 75 minutes. The melt is cooled rapidly by pouring into water. The resulting glass is ground and sieved, and the fraction of particle size less than 45 microns used in the composition. It was exposed to 60 seconds' white light, and the resulting cement was hard, opaque and resistant to water.

EXAMPLE 3

A composition was made up consisting of
0.25 g of the DVPA ester of Example 1
0.02 ml water
0.04 g poly(vinyl phosphonic acid)
0.5 g of the glass of Example 2
0.01 g of light-activated initiator (consisting of CQ+EDMAB+NaTS).

The whole was thoroughly mixed to form a paste, in which the poly(vinyl phosphonic acid) solid was dissolved in a mixture of the water and the ester.

One portion of this composition remained workable for about 30 minutes in normal indoors light. Another portion, exposed to 60 seconds' white light, was immediately stable against water. A further composition (not according to the invention) was made up according to this Example but without the initiators; that composition hardened overnight to a water-stable cement.

EXAMPLE 4

A two paste composition was devised comprising firstly a concentrated solution (80% by mass and hence adequately viscous) of poly(vinyl phosphonic acid) in water, additionally containing CQ+EDMAB+NaTS; and secondly a paste containing the phosphonate ester of Example 1 (0.5 g) and the glass powder (1.0 g) of Example 2. Equal volumes of the two pastes were mixed and on exposure to white light the mixture set to a hard, water stable cement.

We claim:

1. A command-curable composition, comprising an unsaturated phosphonate ester, being equivalent to the reaction product between an unsaturated phosphonic acid and a polyhydric alcohol in the mole ratio of (0.2-2.0) phosphonic acid groups: 1 hydroxyl groups, an initiator, and a cross-linkable polymeric acid capable of being gelled by cations with a valency of at least 2, said acid containing on average one phosphonic acid group per one to three backbone carbon atoms.

2. A composition according to claim 1, wherein said mole ratio is (from 0.5 to 1.5):1.

3. A composition according to claim 1, wherein the hydroxyls in the polyhydric alcohol are interconnected via from two to twenty carbon atoms.

4. A composition according to claim 3, wherein the hydroxyls in the polyhydric alcohol are interconnected via from two to six carbon atoms.

5. A composition according to claim 3, wherein oxygen atoms are interposed in the alcohol.

6. A composition according to claim 5, wherein an oxygen atom is interposed at least every fifth carbon atom.

7. A composition according to claim 1, further comprising any one or more of cation-leachable glass powder, amphoteric or basic metal oxide, poly(vinyl phosphonic acid), and water.

8. A composition according to claim 7, wherein the glass powder is of particles substantially all smaller than 100 microns.

9. A composition according to claim 1, further comprising an inert filler.

10. A pack comprising two separated pastes which when mixed form a composition according to claim 1.

11. A pack comprising the components which when mixed form a composition according to claim 1 so packed that when unpacked and mixed they form the composition.

12. A dental cement comprising a composition according to claim 1.

13. A command-curable composition comprising a partly esterified phosphonic acid having 0.2-5.0 phosphonic acid groups per unsaturated functional esterifying group, an initiator, and a cross-linkable polymeric acid capable of being gelled by cations with a valency of at least 2, said acid containing on average one phosphonic acid group per one to three backbone carbon atoms.

* * * * *